United States Patent
Vogt

(10) Patent No.: US 9,707,312 B2
(45) Date of Patent: *Jul. 18, 2017

(54) PASTE-LIKE BONE CEMENT

(71) Applicant: HERAEUS MEDICAL GMBH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 513 days.

This patent is subject to a terminal disclaimer.

(21) Appl. No.: 13/873,921

(22) Filed: Apr. 30, 2013

(65) Prior Publication Data

US 2013/0310466 A1 Nov. 21, 2013

(30) Foreign Application Priority Data

May 16, 2012 (EP) .................................... 12003855

(51) Int. Cl.
*A61F 13/00* (2006.01)
*A61L 24/04* (2006.01)
*A61L 24/06* (2006.01)

(52) U.S. Cl.
CPC .............. *A61L 24/043* (2013.01); *A61L 24/06* (2013.01)

(58) Field of Classification Search
CPC ......... A61L 24/06; A61L 24/043; C08L 33/10
See application file for complete search history.

(56) References Cited

U.S. PATENT DOCUMENTS

| 4,015,945 | A | 4/1977 | Frankel et al. |
| 6,096,842 | A | 8/2000 | Friese et al. |
| 2003/0086332 | A1 | 5/2003 | Jonsson |
| 2007/0023165 | A1 | 2/2007 | Lakes et al. |
| 2009/0105144 | A1 | 4/2009 | Vogt et al. |
| 2009/0105366 | A1 | 4/2009 | Vogt et al. |
| 2009/0105367 | A1 | 4/2009 | Vogt et al. |
| 2011/0112210 | A1 | 5/2011 | Vogt et al. |
| 2011/0313078 | A1 | 12/2011 | Vogt et al. |
| 2014/0024739 | A1* | 1/2014 | Vogt .............................. 523/116 |
| 2014/0031451 | A1* | 1/2014 | Vogt .............................. 523/116 |

FOREIGN PATENT DOCUMENTS

| DE | 33 20 918 A1 | 12/1983 |
| DE | 195 01 933 A1 | 7/1996 |
| DE | 10 2007 050 763 A1 | 4/2009 |
| DE | 10 2007 052 116 A1 | 4/2009 |
| DE | 10 2007 050 762 B3 | 5/2009 |
| DE | 10 2010 055759 A1 | 7/2011 |
| EP | 0 659 859 A1 | 6/1995 |
| EP | 0 674 888 A1 | 10/1995 |
| GB | 2121811 A | 1/1984 |
| JP | 2003-181270 A | 7/2003 |
| JP | 2009-101159 A | 5/2009 |
| JP | 2009-101160 A | 5/2009 |
| JP | 2011-526171 A | 10/2011 |
| JP | 2012-5829 A | 1/2012 |
| WO | 2005 087850 A1 | 9/2005 |

OTHER PUBLICATIONS

English Translation Office Action JP Patent Application No. 2013-098951.
Pedraza et al., "Reduction in Fixture Time of a Two-Component Structural Acrylic Adhesive", International Journal of Adhesion & Adhesive, vol. 28, pp. 283-290, 2008.
J.D.B Smith, "Kinetic Studies on Anaerobic Initiated Polymerization", Westinghouse Science and Technology Center, Journal of Applied Polymer Science vol. 46, pp. 1-16, (1992).
Yul Bae et al., "The Effect of Saccharin on Curing Times and Bonding Properties of Anaerobic Adhesive", Laboratory of Adhesion & Bio-Composites, pp. 217-221, 2010.
Japanese Office Action dated Jan. 13, 2014.
English Translation of Japanese Office Action dated Jan. 13, 2014.
Patent Examination Report issued in corresponding Australian Application No. 2013205605 on Apr. 3, 2014.
Charnley, J.: "Anchorage of the Femoral Head Prosthesis of the Shaft of the Femur"; J. Bone Joint Surg. vol. 42 B, No. 1, pp. 28-30, Feb. 1960.
Japanese Office Action dated Jan. 15, 2014.
English Translation of Japanese Office Action dated Jan. 15, 2014.

* cited by examiner

*Primary Examiner* — Lakshmi Channavajjala
(74) *Attorney, Agent, or Firm* — Norris McLaughlin & Marcus P.A.

(57) ABSTRACT

Kit for producing a bone cement paste, comprising a paste A and a paste B; paste A comprising at least one monomer for radical polymerization, at least one peroxide polymerization initiator and at least one tertiary amine, at least one amidine or a mixture of a tertiary amine and amidine; paste B comprising at least one monomer for radical polymerization, at least one heavy metal compound as polymerization accelerator, and as polymerization co-accelerator at least one sulfimide, at least one dicarboxylic acid imide or a mixture thereof, at least one of the pastes A and B comprising at least one filling agent that is insoluble in the monomer of paste A and/or the monomer of paste B.

17 Claims, No Drawings

PASTE-LIKE BONE CEMENT

The present invention relates to a kit, the use of the kit for producing a paste for mechanical fixation of articular endoprostheses, for covering skull defects, for filling bone cavities, for femuroplasty, for vertebroplasty, for kyphoplasty, for the manufacture of spacers or for the production of carrier materials for local antibiotics therapy, as well as a form body.

Conventional polymethylmethacrylate bone cements (PMMA bone cements) have been known for decades and are based on the ground-breaking work of Sir Charnley (Charnley, J.: *"Anchorage of the femoral head prosthesis of the shaft of the femur"*; J. Bone Joint Surg. 42 (1960) 28-30). The basic structure of PMMA bone cements has remained the same ever since. PMMA bone cements consist of a liquid monomer component and a powder component. The monomer component generally contains (i) the monomer, methylmethacrylate, and (ii) an activator (e.g. N,N-dimethyl-p-toluidine) dissolved therein. The powder component comprises (i) one or more polymers that are made by polymerisation, preferably by suspension polymerisation, based on methylmethacrylate and co-monomers, such as styrene, methacrylate or similar monomers, (ii) a radioopaquer, and (iii) an initiator, (e.g. dibenzoylperoxide). Mixing the powder component and the monomer component, the polymers of the powder component in the methylmethacrylate swell which generates a dough that can be shaped plastically. Simultaneously, the activator, N,N-dimethyl-p-toluidine, reacts with dibenzoylperoxide which disintegrates and forms radicals in the process. The radicals thus formed trigger the radical polymerisation of the methylmethacrylate. Upon advancing polymerisation of the methylmethacrylate, the viscosity of the cement dough increases until the cement dough solidifies and thus is cured.

The essential disadvantage of the previous PMMA bone cements for the medical user is that the user needs to mix the liquid monomer component and the powder component in a mixing system or in crucibles right before applying the cement. Mixing errors can easily occur in the process and adversely affect the quality of the cement. Moreover, the components must be mixed rapidly. In this context, it is important to mix all of the cement powder and monomer component without forming lumps and prevent the introduction of air bubbles during the mixing process. Unlike manual mixing, the use of vacuum mixing systems prevents the formation of air bubbles in the cement dough to a large extent. Examples of mixing systems are disclosed in patent specifications U.S. Pat. No. 4,015,945, EP-A-0 674 888, and JP 2003-181270. However, vacuum mixing systems necessitate an additional vacuum pump and are therefore relatively expensive. Moreover, depending on the type of cement concerned, a certain waiting time is required after mixing the monomer component and the powder component until the cement dough is tack-free and can be applied. Because of the large variety of errors that can occur while mixing conventional PMMA bone cements, appropriately trained personnel is required for this purpose. The corresponding training is associated with considerable expenses. Moreover, mixing of the liquid monomer component and the powder component is associated with exposure of the user to monomer vapours and particles released from the powder-like cement.

Paste-like polymethylmethacrylate bone cements have been described as an alternative to the conventional powder-liquid polymethylmethacrylate bone cements in unexamined German patent applications DE-A-10 2007 052 116, DE-A-10 2007 050 762, and DE-A-10 2007 050 763. Said bone cements are provided to the user in the form of pre-mixed pastes that are stable during storage. Said pastes each contain one methacrylate monomer for radical polymerisation, one polymer that is soluble in said methacrylate polymer, and one particulate polymer that is insoluble in said methacrylate monomer (since both pastes contain an insoluble particulate polymer, systems of this type are called "symmetrical"). In addition, one of said pastes contains a radical polymerisation initiator, whereas the other paste comprises a polymerisation activator. As a result of the selected composition, the bone cement produced from said pastes possesses sufficiently high viscosity and cohesion in order to withstand the pressure from bleeding until it is fully cured. When the two pastes are mixed, the polymerisation initiator reacts with the accelerator to form radicals that initiate the radical polymerisation of the methacrylate monomers.

The documents listed propose barbiturates in combination with heavy metal ions and halide ions as initiator systems. Moreover, they make mention of the dibenzoylperoxide/tertiary aromatic amine redox initiator system.

EP 0 659 859 A1 discloses an adhesive whose first component contains not only monomers, but also a hydroperoxide, and whose second component contains not only monomers, but also a heavy metal salt and a sulfimide. The use of tertiary amines as co-accelerator is not mentioned therein.

A two-part adhesive composition is also disclosed in DE 33 20 918 A1. The one part of the adhesive contains a polymerisable acrylate or methacrylate, a peroxide, and, if applicable, a sulfimide, and, if applicable, a hydrazine derivative. The second part of the adhesive contains not only a polymerisable acrylate or methacrylate, but also a transition metal salt and, if applicable, an amine as co-accelerator. Some experiments showed that mixtures of methacrylate monomer (ethylene glycol dimethacrylate), cumene hydroperoxide, and saccharine (sulfimide) mixed with mixtures of methacrylate monomer with copper(II) 2-ethylhexanoate and N,N-dimethyl-p-toluidine dissolved therein and stored at room temperature deteriorate in terms of the initiation of the exothermal polymerisation within just a few days at elevated temperature (50° C.). This effect is obviously a result of oxidative decomposition of saccharine through the action of cumene hydroperoxide.

DE 195 01 933 A1 describes an aerobically curing adhesive based on methacrylate monomers with a boiling point above 120° C. Said 2-component adhesive contains a hydroperoxide in one paste and at least one heavy metal compound in the second paste. Sulfimides, tertiary amines, and hydrazine derivatives are proposed as accelerators. The special advantage of said adhesives supposedly is that no tacky layer (dispersion layer) is obtained at the boundary to air due to the use of methacrylate monomers with a boiling point above 120° C. The dispersion layer is formed through interference with the polymerisation due to the effect of atmospheric oxygen and contains not only oligomers and polymers, but unreacted monomers as well. As a result, dispersion layers contacting human tissue can cause tolerability issues.

The present invention was based on the object to overcome the disadvantages of the prior art concerning bone cement systems that are based on at least two pastes.

The present invention was based, in particular, on the object to provide a polymethylmethacrylate bone cement kit based on two pastes for radical polymerisation, whereby the pastes, for as long as they are separated from each other, should be characterised through the highest possible stability against polymerisation (i.e. should show as little tendency to undergo spontaneous polymerisation as possible). Mixing the two pastes is to generate a paste that cures on its own within just a few minutes due to radical polymerisation. In this context, the rate at which radical polymerisation proceeds after the two pastes are mixed is to be as even as possible and, in particular, is to be independent of how long the pastes were stored separate from each other previously.

The present invention was also based on the object to provide a polymethylmethacrylate bone cement kit based on two pastes for radical polymerisation, which cure on their own within just as few minutes after being mixed with each other due to radical polymerisation while forming a polymer that comprises, to the extent possible, no noticeably tacky dispersion layer on its surface.

A kit comprising a paste A and a paste B contributes to a solution meeting the object specified above,
whereby
(a) paste A contains
   (a1) at least one monomer for radical polymerisation with a boiling point below 120° C. at a pressure of 1,013 mbar;
   (a2) at least one peroxide as polymerisation initiator; and
   (a3) as polymerisation co-accelerator, at least one tertiary amine, at least one amidine or a mixture of at least one tertiary amine and at least one amidine; and
(b) paste B contains
   (b1) at least one monomer for radical polymerisation with a boiling point below 120° C. at a pressure of 1,013 mbar;
   (b2) at least one heavy metal compound as polymerisation accelerator; and
   (b3) as polymerisation co-accelerator, at least one sulfimide, at least one dicarboxylic acid imide or a mixture of at least one sulfimide and at least one dicarboxylic acid imide;
whereby at least one of the pastes A and B contains, as component (a4) and/or (b4), at least one filling agent that is insoluble in (a1) and/or (b1), respectively.

The invention is based, amongst other factors, on the surprising finding that polymers without tackiness at the surface can be produced from pastes including the peroxide/sulfimide/tertiary amine initiator system even when methacrylate monomers with a boiling point of less than 120° C. are used, which is in contrast to the teaching of DE 195 01 933 A2. This renders said polymers tolerable, even in contact with human tissue, provided suitable monomers are used.

According to the invention, a "kit" shall be understood to be a system made up of at least two components. Although reference to two components (i.e. paste A and paste B) is made in the following, the kit can just as well contain more than two components, for example three, four, five or more than five components, according to need. The individual components preferably are provided to be packaged separate from each other such that the ingredients of the one kit component do not contact the ingredients of another kit component. Accordingly, it is feasible, for example, to package the respective kit components separate from each other and to store them together in a reservoir container.

Paste A contains, as component (a1), a monomer for radical polymerisation with a boiling point of less than 120° C. at a pressure of 1,013 mbar, whereby this preferably concerns a monomer that is liquid at a temperature of 25° C. and a pressure of 1,013 mbar.

Preferably, the monomer (a1) for radical polymerisation is a methacrylate monomer, in particular a methacrylic acid ester. Preferably, the methacrylic acid ester (a1) is a monofunctional methacrylic acid ester. Preferably, said substance is hydrophobic. The use of hydrophobic monofunctional methacrylic acid esters (a1) allows later enlargement of the volume of the bone cement due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The esters preferably are alkyl esters. According to the invention, cycloalkyl esters are also included in alkyl esters. According to a preferred embodiment, the alkyl esters are esters of methacrylic acid and alcohols comprising 1 to 20 carbon atoms, more preferably 1 to 10 carbon atoms, even more preferably 1 to 6 carbon atoms, and particularly preferably 1 to 4 carbon atoms. The alcohols can be substituted or non-substituted and preferably are non-substituted. Moreover, the alcohols can be saturated or unsaturated and preferably are saturated.

According to a particularly preferred embodiment, the monomer (a1) for radical polymerisation is a methacrylic acid methylester, methacrylic acid ethylester or a mixture of said two monomers.

The monomer (a1) for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer (a1) for radical polymerisation is preferably characterised in that an aqueous solution of the monomer (a1) for radical polymerisation has a pH in the range of 5 to 9, preferably in the range of 5.5 to 8.5, even more preferably in the range of 6 to 8, and particularly preferably in the range of 6.5 to 7.5.

Paste A preferably contains 15 to 85% by weight, more preferably 20 to 70% by weight, even more preferably 25 to 60% by weight, and particularly preferably 25 to 50% by weight, each relative to the total weight of paste A, of the at least one monomer (a1) for radical polymerisation.

Paste A further contains, as component (a2), at least one peroxide, which preferably has a half-life >10 hours, particularly preferably >24 hours, and even more preferably >48 hours, each measured at 70° C. Determining the half-life involves determining the peroxide content through iodine titration, in which the iodide ions are oxidised to iodine through the peroxide.

It is particularly preferred for peroxide (a2) to be selected from the group consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, di-t-butylperoxide, dicumylperoxide, and t-butyl-cumyl-peroxide.

Preferably, paste A contains an amount of the at least one peroxide (a2) in a range of 0.01 to 10% by weight, more preferably in a range of 0.1 to 8% by weight, and even more preferably in a range of 1 to 5% by weight, each relative to the total weight of paste A.

Paste A further contains, as component (a3), at least one tertiary amine, at least one amidine or a mixture of at least one tertiary amine and at least one amidine as polymerisation co-accelerator.

The tertiary amine preferably is an amine selected from the group consisting of tributylamine, triethanolamine, N,N-dimethyl-p-toluidine, N,N-bis(2-hydroxy-ethyl)-p-toluidine, and N,N-dimethylaniline. The combination of N,N-dimethyl-p-toluidine and N,N-bis(2-hydroxyethyl)-p-toluidine is particularly advantageous. This combination allows the curing behaviour of mixed paste C to be controlled very well through variation of the ratio of N,N-dimethyl-p-toluidine and N,N-bis(2-hydroxyethyl)-p-toluidine.

An amidine can be used as base just as well in place of the tertiary amine (or in combination with the tertiary amine). In this context, 1,8-diazabicyclo[5.4.0]undec-7-ene (DBU) and 1,5-diazabicyclo(4.3.0)non-5-ene (DBN) are particularly preferred.

Preferably, paste A contains an amount of the polymerisation co-accelerator (a3) in a range of 0.1 to 20% by weight, more preferably in a range of 0.5 to 10% by weight, and even more preferably in a range of 1 to 5% by weight, each relative to the total weight of paste A.

Paste B also contains, as component (b1), a monomer for radical polymerisation with a boiling point below 120° C. at a pressure of 1,013 mbar, whereby this preferably concerns a monomer that is liquid at a temperature of 25° C. and a pressure of 1,013 mbar. The monomer (b1) for radical polymerisation contained in a kit can be identical to or different from the monomer (a1) for radical polymerisation, whereby it is preferred for the monomer (a1) for radical polymerisation and the monomer (b1) for radical polymerisation to be identical.

The monomer (b1) for radical polymerisation preferably is a methacrylate monomer, in particular a methacrylic acid ester. Preferably, the methacrylic acid ester (b1) is a monofunctional methacrylic acid ester. Preferably, said substance is hydrophobic. The use of hydrophobic monofunctional methacrylic acid esters (b1) allows later enlargement of the volume of the bone cement due to the uptake of water and thus damage to the bone to be prevented. According to a preferred embodiment, the monofunctional methacrylic acid ester is hydrophobic if it contains no further polar groups aside from the ester group. The monofunctional hydrophobic methacrylic acid ester preferably comprises no carboxyl groups, hydroxyl groups, amide groups, sulfonic acid groups, sulfate groups, phosphate groups or phosphonate groups.

The esters preferably are alkyl esters. According to the invention, cycloalkyl esters are also included in alkyl esters. According to a preferred embodiment, the alkyl esters are esters of methacrylic acid and alcohols comprising 1 to 20 carbon atoms, more preferably 1 to 10 carbon atoms, even more preferably 1 to 6 carbon atoms, and particularly preferably 1 to 4 carbon atoms. The alcohols can be substituted or non-substituted and preferably are non-substituted. Moreover, the alcohols can be saturated or unsaturated and preferably are saturated.

According to a particularly preferred embodiment, the monomer (b1) for radical polymerisation is a methacrylic acid methylester, methacrylic acid ethylester or a mixture of said two monomers.

According to a further particularly preferred embodiment, the monomer (b1) for radical polymerisation is not a bisphenol A-derived methacrylic acid ester.

The monomer (b1) for radical polymerisation used according to the invention preferably has a molar mass of less than 1,000 g/mol. This also comprises monomers for radical polymerisation that are components of a mixture of monomers, whereby at least one of the monomers for radical polymerisation of the mixture of monomers has a defined structure with a molar mass of less than 1,000 g/mol.

The monomer (b1) for radical polymerisation is characterised in that an aqueous solution of the monomer (b1) for radical polymerisation has a pH in the range of 5 to 9, preferably in the range of 5.5 to 8.5, even more preferably in the range of 6 to 8, and particularly preferably in the range of 6.5 to 7.5.

Paste B preferably contains 15 to 85% by weight, more preferably 20 to 70% by weight, even more preferably 25 to 60% by weight, and particularly preferably 25 to 50% by weight, each relative to the total weight of paste B, of the at least one monomer (b1) for radical polymerisation.

Paste B further contains as component (b2) at least one heavy metal compound as polymerisation accelerator, whereby the heavy metal compound can be a heavy metal salt or a heavy metal complex. According to a particularly preferred embodiment, the heavy metal compounds (b2) are compounds of metals that can change their oxidation state. Copper (II), iron (II), iron (III), manganese (II), manganese (III), cobalt (II), and cobalt (III) compounds are preferred according to the invention in this context with copper(II) compounds being particularly preferred. Heavy metal compounds (b2) that are particularly preferred in this context are selected from the group consisting of copper(II) hydroxide, copper(II) metharylate, copper(II) acetylacetonate, copper (II) 2-ethyl-hexanoate, cobalt(II) hydroxide, cobalt(II) 2-ethyl-hexanoate, and basic copper(II) carbonate.

Preferably, paste B contains an amount of the heavy metal compound (b2) in a range of 0.0005 to 0.5% by weight, more preferably in a range of 0.001 to 0.05% by weight, and particularly preferably in a range of 0.001 to 0.01% by weight, each relative to the total weight of paste B.

Paste B further contains as component (b3) at least one sulfimide, at least one dicarboxylic acid imide or a mixture of at least one sulfimide and at least one dicarboxylic acid imide as polymerisation co-accelerator, whereby saccharine is a particularly preferred sulfimide and phthalimide, maleimide, and succinimide are particularly preferred dicarboxylic acid imides. In addition, the use of tetracarboxylic acid diimides, such as pyromellithic acid diimide, is also preferred.

Preferably, paste B contains an amount of the polymerisation co-accelerator (b2) in a range of 0.1 to 10% by weight, more preferably in a range of 0.5 to 8% by weight, and particularly preferably in a range of 1 to 5% by weight, each relative to the total weight of paste B.

The kit according to the invention is characterised further in that at least one of the pastes A and B contains, as component (a4) and/or (b4), at least one filling agent that is insoluble in (a1) and/or (b1), respectively. Provided one of the two pastes contains an insoluble filling agent and the other paste contains no insoluble filling agent at all or contains a negligible amount of insoluble filling agent as compared to the amount present in the other paste, the kit is called "asymmetrical". In contrast, a so-called "symmetrical" kit has approximately comparable amounts of the insoluble filling agent present in both pastes.

The filling agent (a4) (in case of paste A) and/or (b4) (in case of paste B) is a solid substance at room temperature and capable of increasing the viscosity of the mixture composed of the remaining ingredients contained in paste A and/or paste B, respectively. The filling agent (a4) and/or (b4) should be biocompatible.

According to a preferred embodiment, the filling agent (a4) and/or (b4) is selected from polymers, inorganic salts, inorganic oxides, metals, and metal alloys.

Preferably, the filling agent (a4) and/or (b4) is particulate. According to a particularly preferred embodiment, the filling agent (a4) and/or (b4) has an average particle size in the range of 10 nm to 100 µm and particularly preferably in the range of 100 nm to 10 µm. The average particle size shall be understood herein to mean a size range that applies to at least 90 percent of the particles.

In the scope of the invention, the term, polymers, shall include both homopolymers and copolymers.

The polymer that can be used as filling agent (a4) and/or (b4) preferably is a polymer with a mean (by weight) molar mass of at least 150,000 g/mol. The specification of the molar mass refers to the molar mass determined by viscosimetry. The polymer can, for example, be a polymer or copolymer of a methacrylic acid ester. According to a particularly preferred embodiment, the at least one polymer is selected from the group consisting of polymethacrylic acid methylester (PMMA), polymethacrylic acid ethylester (PMAE), polymethacrylic acid propylester (PMAP), polymethacrylic acid isopropylester, poly(methylmethacrylate-co-methylacrylate), and poly(styrene-co-methylmethacrylate). However, the polymer can just as well be selected from the group consisting of polyethylene, polypropylene or polybutadiene. Moreover, the polymer can be cross-linked or non-cross-linked with cross-linked polymers being preferred. In this context, the cross-linking is effected through a difunctional compound. The difunctional compound can be selected, for example, from the group consisting of alkylene glycol dimethacrylates. An expedient cross-linker is, for example, ethylene glycol dimethacrylate.

The inorganic salt that can be used as filling agent (a4) and/or (b4) can be a salt that is soluble or insoluble in the monomer (a1) and/or (b1) for radical polymerisation. Preferably, the inorganic salt is a salt of an element selected from the second main group of the periodic system of elements. According to a preferred embodiment, the inorganic salt is a calcium, strontium or barium salt. According to a particularly preferred embodiment, the inorganic salt is calcium sulfate, barium sulfate or calcium carbonate.

The inorganic oxide that can be used as filling agent (a4) and/or (b4) can preferably be a metal oxide. According to a preferred embodiment, the inorganic oxide is a transition metal oxide. According to a particularly preferred embodiment, the inorganic oxide is titanium dioxide or zirconium dioxide.

The metal that can be used as filling agent (a4) and/or (b4) can, for example, be a transition metal. According to a preferred embodiment, the metal is tantalum or tungsten.

The metal alloy that can be used as filling agent (a4) and/or (b4) is an alloy of at least two metals. Preferably, the alloy contains at least one transition metal. According to a particularly preferred embodiment, the alloy comprises at least tantalum or tungsten. The alloy can also be an alloy of tantalum and tungsten.

The filling agent (a4) and/or (b4) is insoluble in the monomer (a1) and/or (b1) for radical polymerisation, respectively. According to the invention, the filling agent (a4) and/or (b4) is insoluble in the at least one monomer (a1) and/or (b1) for radical polymerisation, if the solubility of the filling agent (a4) and/or (b4) in the monomer (a1) and/or (b1) for radical polymerisation at a temperature of 25° C. is less than 50 g/l, preferably is less than 25 g/l, more preferably is less than 10 g/l, and even more preferably is less than 5 g/l.

It is particularly preferred according to the invention that the at least one polymer that is insoluble in (a1) and/or (b1) is selected from the group consisting of cross-linked poly (methylmethacrylate-co-methylacrylate), cross-linked poly (methylmethacrylate), and a mixture of said two polymers.

Moreover, according to the invention, paste A, paste B or paste A and paste B, though particularly preferably paste A and paste B, can contain a polymer (a5) and/or (b5) that is soluble in (a1) and/or (b1), respectively. According to the invention, said polymer (a5) and/or (b5) is soluble in the polymerisable monomer contained in the paste that contains the soluble polymer as well, if at least 10 g/l, preferably at least 25 g/l, more preferably at least 50 g/l, and particularly preferably at least 100 g/l of the polymer dissolve in said polymerisable monomer. The polymer (a5) and/or (b5) that is soluble in the polymerisable monomer (a1) and/or (b1), respectively, can be a homopolymer or a copolymer. Said polymer (a5) and/or (b5) preferably is a polymer with a mean (by weight) molar mass of at least 150,000 g/mol. The polymer (a5) and/or (b5) can, for example, be a polymer or copolymer of a methacrylic acid ester. According to a particularly preferred embodiment, the at least one polymer (a5) and/or (b5) is selected from the group consisting of polymethacrylic acid methylester (PMMA), polymethacrylic acid ethylester (PMAE), polymethacrylic acid propylester (PMAP), polymethacrylic acid isopropylester, poly (methylmethacrylate-co-methylacrylate), and poly(styrene-co-methylmethacrylate).

The amount of the polymer (a5) and/or (b5) that is soluble in the monomer (a1) and/or (b1) for radical polymerisation, respectively, that is present in the paste containing said polymer depends on whether or not the corresponding paste contains a filling agent (a4) and/or (b4) that is insoluble in the monomer (a1) and/or (b1) for radical polymerisation, respectively. Usually, the amount of the polymer (a5) and/or (b5) that is soluble in the monomer (a1) and/or (b1) for radical polymerisation, respectively, that is present in the paste containing said polymer is in a range of 1 to 85% by weight, relative to the total weight of the paste containing said soluble polymer.

Pastes A and B can contain further components aside from the components explained above. Said further components can each be present either in paste A, in paste B or in paste A and paste B.

According to a preferred embodiment, at least one radio-opaquer is present in at least one of the pastes A and B. The radio-opaquer can be a common radio-opaquer in this field. Suitable radio-opaquers can be soluble or insoluble in the monomer (a1) for radical polymerisation or the monomer (b1) for radical polymerisation. The radio-opaquer is preferably selected from the group consisting of metal oxides (such as, for example, zirconium oxide), barium sulfate, toxicologically acceptable heavy metal particles (such as, for example, tantalum), ferrite, magnetite (supramagnetic magnetite also, if applicable), and biocompatible calcium salts. Said radio-opaquers preferably have a mean particle diameter in the range of 10 nm to 500 µm. Moreover, conceivable radio-opaquers also include esters of 3,5-bis (acetamido)-2,4,6-triiodobenzoic acid, gadolinium compounds, such as gadolinium chelate involving the esters of 1,4,7,10-tetraazacyclododecan-1,4,7,10-tetraacetic acid (DOTA).

According to another preferred embodiment, at least one of the pastes A and B contains at least one colourant. The colourant can be a common colourant in this field and preferably can be a food colourant. Moreover, the colourant can be soluble or insoluble in the at least one monomer (a1) for radical polymerisation or the at least one monomer (a2) for radical polymerisation. According to a particularly preferred embodiment, the colourant is selected from the group consisting of E101, E104, E132, E141 (chlorophyllin), E142, riboflavin, and lissamine green. According to the invention, the term, colourant, shall also include colour varnishes, such as, for example, colour varnish green, the aluminium salt of a mixture of E104 and E132.

According to another preferred embodiment, at least one of the pastes A and B contains at least one pharmaceutical agent. The at least one pharmaceutical agent can be present in at least one of pastes A and B in dissolved or suspended form.

The pharmaceutical agent can preferably be selected from the group consisting of antibiotics, antiphlogistic agents, steroids, hormones, growth factors, bisphosphonates, cytostatic agents, and gene vectors. According to a particularly preferred embodiment, the at least one pharmaceutical agent is an antibiotic.

Preferably, the at least one antibiotic is selected from the group consisting of aminoglyoside antibiotics, glycopeptide antibiotics, lincosamide antibiotics, gyrase inhibitors, carbapenems, cyclic lipopeptides, glycylcyclines, oxazolidones, and polypeptide antibiotics.

According to a particularly preferred embodiment, the at least one antibiotic is a member selected from the group consisting of gentamicin, tobramycin, amikacin, vancomycin, teicoplanin, dalbavancin, lincosamine, clindamycin, moxifloxacin, levofloxacin, ofloxacin, ciprofloxacin, doripenem, meropenem, tigecycline, linezolide, eperezolide, ramoplanin, metronidazole, tinidazole, omidazole, and colistin, as well as salts and esters thereof.

Accordingly, the at least one antibiotic can be selected from the group consisting of gentamicin sulfate, gentamicin hydrochloride, amikacin sulfate, amikacin hydrochloride, tobramycin sulfate, tobramycin hydrochloride, clindamycin hydrochloride, lincosamine hydrochloride, and moxifloxacin.

The at least one antiphlogistic agent is preferably selected from the group consisting of non-steroidal antiphlogistic agents and glucocorticoids. According to a particularly preferred embodiment, the at least one antiphlogistic agent is selected from the group consisting of acetylsalicylic acid, ibuprofen, diclofenac, ketoprofen, dexamethasone, prednisone, hydrocortisone, hydrocortisone acetate, and fluticasone.

The at least one hormone is preferably selected from the group consisting of serotonin, somatotropin, testosterone, and estrogen.

Preferably, the at least one growth factor is selected from the group consisting of Fibroblast Growth Factor (FGF), Transforming Growth Factor (TGF), Platelet Derived Growth Factor (PDGF), Epidermal Growth Factor (EGF), Vascular Endothelial Growth Factor (VEGF), insulin-like growth factors (IGF), Hepatocyte Growth Factor (HGF), Bone Morphogenetic Protein (BMP), interleukin-1B, interleukin 8, and nerve growth factor.

The at least one cytostatic agent is preferably selected from the group consisting of alkylating agents, platinum analogues, intercalating agents, mitosis inhibitors, taxanes, topoisomerase inhibitors, and antimetabolites.

The at least one bisphosphonate is preferably selected from the group consisting of zoledronate and aledronate.

According to another preferred embodiment, at least one of the pastes A and B contains at least one biocompatible elastomer. Preferably, the biocompatible elastomer is particulate. Preferably, the biocompatible elastomer is soluble in the at least one monomer (a1) for radical polymerisation or the at least one monomer (b1) for radical polymerisation. The use of butadiene as biocompatible elastomer has proven to be particularly well-suited.

According to another preferred embodiment, at least one of the pastes A and B contains at least one monomer with adsorption groups. The adsorption group can, for example, be an amide group. Accordingly, the monomer with adsorption group can, for example, be methacrylic acid amide. Using at least one monomer with adsorption groups would allow the binding of the bone cement to articular endoprostheses to be influenced in a targeted manner.

According to another preferred embodiment, at least one of the pastes A and B contains at least one stabiliser. The stabiliser should be suitable to prevent spontaneous polymerisation of the monomers (a1) and/or (b1) for polymerisation that are present in pastes A and B. Moreover, the stabiliser should not undergo interfering interactions with the other components contained in the pastes. Stabilisers of said type are known according to the prior art. According to a preferred embodiment, the stabiliser is 2,6-di-tert-butyl-4-methylphenol and/or 2,6-di-tert-butylphenol.

According to a first particular refinement of the kit according to the invention, the kit is an "asymmetrical" kit. It is preferred in this context that paste A contains 20 to 70% by weight, particularly preferably 25 to 60% by weight, even more preferably 30 to 55% by weight, and most preferably 34 to 47% by weight, each relative to the total weight of paste A, of the filling agent (a4) that is insoluble in (a1), and paste B contains less than 5% by weight, particularly preferably less than 1% by weight, even more preferably less than 0.1% by weight, and yet more preferably less than 0.01% by weight, each relative to the total weight of paste B, of the filling agent (b4) that is insoluble in (b1), whereby it is most preferred that paste B contains no filling agent (b4) that is insoluble in (b1) at all.

Moreover, in the context of said first particular refinement of the kit according to the invention, it is preferred that paste A contains an amount of a polymer (a5) that is soluble in (a1) in a range of 1 to 25% by weight, particularly preferably in a range of 2 to 20% by weight, even more preferably in a range of 2 to 18% by weight, and most preferably in a range of 3 to 16% by weight, each relative to the total weight of paste A, and paste B contains an amount of a polymer (b5) that is soluble in (b1) in a range of 25 to 85% by weight, particularly preferably in a range of 35 to 85% by weight, even more preferably in a range of 40 to 80% by weight, and most preferably in a range of 50 to 75% by weight, each relative to the total weight of paste B.

Moreover, it is preferred in the context of said first particular refinement of the kit according to the invention that the weight ratio of filling agent (b4) that is insoluble in (b1) to the at least one polymer (b5) that is soluble in (b1) is no more than 0.2, more preferably no more than 0.15, even more preferably no more than 0.1, yet more preferably no more than 0.05, particularly preferably no more than 0.02, and even more particularly preferably is equal to 0.

According to a second particular refinement of the kit according to the invention, the kit is a "symmetrical" kit. It is preferred in this context that paste A contains 15 to 85% by weight, particularly preferably 15 to 80% by weight, and even more preferably 20 to 75% by weight, each relative to the total weight of paste A, of the filling agent (a4) that is insoluble in (a1), and paste B contains 15 to 85% by weight, particularly preferably 15 to 80% by weight, and even more preferably 20 to 75% by weight, each relative to the total weight of paste B, of the filling agent (b4) that is insoluble in (b1).

Moreover, in the context of said second particular refinement of the kit according to the invention, it is preferred that paste A contains an amount of a polymer (a5) that is soluble in (a1) in a range of 5 to 50% by weight, particularly preferably in a range of 10 to 40% by weight, and even more preferably in a range of 20 to 30% by weight, each relative to the total weight of paste A, and/or paste B contains an amount of a polymer (b5) that is soluble in (b1) in a range of 5 to 50% by weight, particularly preferably in a range of 10 to 40% by weight, and even more preferably in a range of 20 to 30% by weight, each relative to the total weight of paste B.

According to the invention, the purpose of the kit containing at least pastes A and B is the production of bone cement.

For this purpose, the at least two pastes A and B are mixed with each other, upon which another paste, paste C, is obtained.

The mixing ratio preferably is 0.5 to 1.5 parts by weight of paste A and 0.5 to 1.5 parts by weight of paste B. According to a particularly preferred embodiment, the fraction of paste A is 30 to 70% by weight and the fraction of paste B is 30 to 70% by weight, each relative to the total weight of pastes A and B, respectively.

The mixing process can involve common mixing devices, for example a static mixer or a dynamic mixer.

The mixing process can proceed in a vacuum. However, the use of the initiator system according to the invention also allows for mixing of pastes A and B in the absence of a vacuum without adverse effect on the properties of the bone cement.

Paste C that is ultimately obtained after mixing the pastes of the kit is tack-free according to the ISO 5833 standard and can be processed without delay.

The bone cement generated from paste C by curing attains high strength approximately 3 to 15 minutes after mixing the pastes contained in the kit.

According to a preferred embodiment, the kit according to the invention can be used for mechanical fixation of articular endoprostheses, for covering skull defects, for filling bone cavities, for femuroplasty, for vertebroplasty, for kyphoplasty, for the manufacture of spacers, and for the production of carrier materials for local antibiotics therapy.

In this context, the term, "spacer", shall be understood to mean implants that can be used temporarily in the scope of the two-step exchange of prostheses in septic revision surgeries.

Carrier materials for local antibiotics therapy can be provided as spheres or sphere-like bodies or as bean-shaped bodies. Besides, it is also feasible to produce rod-shaped or disc-shaped carrier materials that contain bone cement made from the kit according to the invention. Moreover, the carrier materials can also be threaded onto absorbable or non-absorbable suture material in a bead-like manner.

The uses according to the invention of bone cement described above are known from the literature and have been described therein on numerous occasions.

According to the invention, the kit is used for the above-described uses in that, preferably, the pastes contained in the kit are mixed with each other to produce a paste that is then used in the above-described uses just like pastes known from the prior art.

A contribution to meeting the objects specified above is also made by a form body obtained through polymerisation of the polymerisable composition according to the invention or through polymerisation of a paste that is can be obtained through mixing paste A and paste B of the kit according to the invention. Form bodies according to the scope of the present invention can be any three-dimensional bodies, in particular the "spacers" described above.

The invention shall be illustrated through the examples described in the following, though without limiting the scope of the invention.

EXAMPLES

Pastes A of examples A1-21 were produced by simple mixing of the components. The pastes thus formed were then stored over night at room temperature.

| | Paste A | | | | | | | | |
|---|---|---|---|---|---|---|---|---|---|
| | Composition of pastes A | | | | | | | | |
| Example no. | CH [g] | BH [g] | EG [g] | MA [g] | MMA [g] | PL1 [g] | PL2 [g] | ZrO$_2$ [g] | Rod [mg] |
| A1 | 0.50 | 0.8 | 0.1 | 0.4 | 17.7 | 5.6 | 15.5 | 4.8 | 20 |
| A2 | 0.50 | 1.0 | 0.1 | 0.4 | 17.7 | 5.6 | 15.5 | 4.8 | 20 |
| A3 | 0.50 | 1.2 | 0.4 | 0.4 | 17.7 | 5.6 | 15.5 | 4.8 | 20 |
| A4 | 0.10 | 1.2 | 0.4 | 0.4 | 17.7 | 5.6 | 15.5 | 4.8 | 20 |
| A5 | 0.10 | 1.2 | 0.7 | 0.4 | 17.7 | 5.6 | 15.5 | 4.8 | 20 |
| A6 | 0.10 | 1.2 | 1.0 | 0.4 | 17.7 | 5.6 | 15.5 | 4.8 | 20 |
| A7 | 0.10 | 1.2 | 1.0 | 0.4 | 17.7 | 5.6 | 15.5 | 4.8 | 20 |
| A8 | 0.05 | 1.2 | 0.1 | 0.4 | 17.7 | 5.6 | 15.5 | 4.8 | 20 |
| A9 | 0.05 | 2.0 | 0.1 | 0.4 | 17.7 | 5.6 | 15.5 | 4.8 | 20 |
| A10 | 0.10 | 2.0 | 0.1 | 0.4 | 17.7 | 5.6 | 15.5 | 4.8 | 20 |
| A11 | 0.05 | 1.2 | 0.7 | 0.4 | 17.7 | 5.6 | 15.5 | 4.8 | 20 |
| A12 | 0.05 | 0.6 | 0.7 | 0.4 | 17.7 | 5.6 | 15.5 | 4.8 | 20 |

Paste A (continued)

| | CH | BH | DM | EG | MA | MMA | PL1 | PL2 | ZrO₂ | Rod |
|---|---|---|---|---|---|---|---|---|---|---|
| A13 | 0.05 | 1.2 | 1.3 | 0.4 | | 17.7 | 5.6 | 15.5 | 4.8 | 20 |
| A14 | 0.20 | 2.0 | 0.1 | 0.4 | | 17.7 | 5.6 | 15.5 | 4.8 | 20 |

| Example no. | CH [g] | BH [g] | DM [g] | EG [g] | MA [g] | MMA [g] | PL1 [g] | PL2 [g] | ZrO₂ [g] | Rod [mg] |
|---|---|---|---|---|---|---|---|---|---|---|
| A15 | 0.05 | 1.6 | 0.4 | 0.1 | 0.4 | 17.7 | 5.6 | 15.5 | 4.8 | 20 |
| A16 | 0.05 | 0.8 | 0.4 | 0.1 | 0.4 | 17.7 | 5.6 | 15.5 | 4.8 | 20 |
| A17 | 0.10 | 1.6 | 0.4 | 0.1 | 0.4 | 17.7 | 5.6 | 15.5 | 4.8 | 20 |
| A18 | 0.05 | 1.4 | 0.6 | 0.1 | 0.4 | 17.7 | 5.6 | 15.5 | 4.8 | 20 |
| A19 | 0.05 | 1.2 | 0.8 | 0.1 | 0.4 | 17.7 | 5.6 | 15.5 | 4.8 | 20 |
| A20 | 0.05 | 1.4 | 0.6 | 0.1 | 0.4 | 17.7 | 5.6 | 15.5 | 4.8 | 20 |
| A21 | 0.05 | 1.4 | 0.6 | 0.1 | 0.4 | 17.7 | 5.6 | 15.5 | 4.8 | 20 |

CH: Cumene hydroperoxide
BH: N,N-Bis-(2-hydroxyethyl)-p-toluidine
DM: N,N-Dimethyl-p-toluidine
EG: Ethylene glycol dimethacrylate
MA: Methacrylamide
MMA: Methylmethacrylate
PL1: linear poly(methylmethacrylate-co-methylacrylate), MW < 500,000 g/mol
PL2: particulate, insoluble, cross-linked polymethylmethacrylate
ZrO₂: Zirconium dioxide
Rod: 2,6-Di-t-butyl-4-methyl-phenol Pastes B of examples B1-21 were produced by simple mixing of the components. The pastes thus formed were then stored over night at room temperature.

Paste B

Composition of pastes B

| Example no. | SAC [g] | CuOct [mg] | MMA [g] | PL1 [g] | Gentamicin sulfate [g] | Rod [mg] |
|---|---|---|---|---|---|---|
| B1 | 1.0 | 25 | 21.2 | 17.5 | — | 35 |
| B2 | 1.0 | 25 | 21.2 | 17.5 | — | 35 |
| B3 | 1.0 | 40 | 21.2 | 17.5 | — | 35 |
| B4 | 1.0 | 40 | 21.2 | 17.5 | — | 35 |
| B5 | 1.0 | 45 | 21.2 | 17.5 | — | 35 |
| B6 | 1.0 | 45 | 21.2 | 17.5 | — | 35 |
| B7 | 1.0 | 45 | 21.2 | 17.5 | — | 35 |
| B8-B19 | 1.0 | 55 | 21.2 | 17.5 | — | 35 |
| B20 | 1.0 | 55 | 21.2 | 17.5 | 1.2 | 35 |
| B21 | 1.0 | 55 | 21.2 | 17.5 | 2.4 | 35 |

SAC: Saccharine
CuOct: Copper(II)-2-ethylhexanoate
MMA: Methylmethacrylate
PL1: linear poly(methylmethacrylate-co-methylacrylate), MW < 500,000 g/mol
Rod: 2,6-Di-t-butyl-4-methyl-phenol Pastes A and B of examples A1-21 and B1-21 were mixed with each other at a weight ratio of 1:1. This immediately resulted in pastes C that were tack-free and cured after 4-15 minutes.

The mixed pastes C produced from pastes A and B of examples 1-21 (weight ratio of paste A to paste B of 1:1) were used to produce strip-shaped test bodies with dimensions of (75 mm×10 mm×3.3 mm) for the assay of bending strength and flexural modulus and cylindrical test bodies (diameter 6 mm, height 12 mm) were used for the assay of compressive strength. The test bodies were then stored for 24 hours on air at 23±1° C. Then the 4-point flexural strength, flexural modulus, and the compressive strength of the test bodies were determined using a Zwick universal testing device.

| Pastes C | Pastes C | Composition of Pastes C | 4-point flexural strength [MPa] | Flexural modulus [MPa] | Compressive strength [MPa] |
|---|---|---|---|---|---|
| P1225 | C1 | A1 + B1 | 60.1 ± 3.7 | 2346 ± 183 | 81.2 ± 6.0 |
| P1227 | C2 | A2 + B2 | 60.9 ± 3.5 | 2409 ± 113 | 92.4 ± 3.7 |
| P1232 | C3 | A3 + B3 | 62.8 ± 2.2 | 2484 ± 26 | 88.2 ± 4.0 |
| P1233 | C4 | A4 + B4 | 62.9 ± 2.6 | 2509 ± 86 | 89.7 ± 3.7 |
| P1234 | C5 | A5 + B5 | 64.7 ± 1.3 | 2593 ± 74 | 93.6 ± 3.2 |
| P1235 | C6 | A6 + B6 | 64.6 ± 1.5 | 2533 ± 25 | 94.3 ± 2.3 |
| P1236 | C7 | A7 + B7 | 60.9 ± 3.7 | 2362 ± 96 | 95.1 ± 2.0 |
| P1238 | C8 | A8 + B8 | 60.4 ± 1.5 | 2380 ± 52 | 91.5 ± 2.3 |
| P1240 | C9 | A9 + B9 | 60.2 ± 0.6 | 2407 ± 27 | 86.7 ± 4.0 |
| P1242 | C10 | A10 + B10 | 64.3 ± 1.1 | 2667 ± 103 | 100.8 ± 3.4 |
| P1244 | C11 | A11 + B11 | 60.2 ± 1.8 | 2470 ± 43 | 89.2 ± 2.9 |
| P1245 | C12 | A12 + B12 | 58.7 ± 1.3 | 2382 ± 38 | 78.1 ± 3.7 |
| P1246 | C13 | A13 + B13 | 55.0 ± 1.8 | 2186 ± 96 | 89.1 ± 4.1 |
| P1248 | C14 | A14 + B14 | 63.5 ± 0.8 | 2473 ± 26 | 88.8 ± 5.8 |
| P1249 | C15 | A15 + B15 | 57.6 ± 1.9 | 2229 ± 100 | 85.0 ± 3.0 |
| P1250 | C16 | A16 + B16 | 67.8 ± 2.6 | 2618 ± 94 | 97.6 ± 4.0 |
| P1251 | C17 | A17 + B17 | 67.1 ± 3.0 | 2969 ± 131 | 92.6 ± 3.1 |
| P1252 | C18 | A18 + B18 | 65.0 ± 1.7 | 2462 ± 67 | 91.7 ± 1.3 |
| P1253 | C19 | A19 + B19 | 67.1 ± 2.6 | 2569 ± 100 | 85.1 ± 2.6 |
| P1254 | C20 | A20 + B20 | 58.1 ± 2.2 | 2278 ± 93 | 80.1 ± 2.8 |
| P1255 | C21 | A21 + B21 | 54.4 ± 2.5 | 2272 ± 68 | 80.4 ± 1.7 |

Moreover, further pastes B analogous to paste B20 but containing vancomycin hydrochloride, clindamycin hydrochloride, daptomycin, and octenidine dihydrochloride instead of gentamicin sulfat were produced. After these pastes B were mixed with paste A20 at a weight ratio of 1:1, the mixed pastes C showed similar curing behaviour as the combination of paste A20 and paste B20 at a weight ratio of 1:1.

Moreover, pastes were produced using barium sulfate instead of zirconium dioxide. Said pastes had a similar curing behaviour as the pastes C produced from pastes A1-21 and B1-21.

Furthermore, pastes A were produced analogous to example A1 using t-butyl-hydroperoxid, t-amyl-hydroperoxide, and dicumyl-peroxide instead of cumene-hydroperoxide. After these pastes A were mixed with paste B1 at a weight ratio of 1:1, the mixed pastes showed similar behaviour as the combination of pastes A1 and paste B1.

The invention claimed is:

1. A kit comprising a paste A and a separate paste B, wherein
   (a) paste A contains
      (a1) at least one monomer for radical polymerization with a boiling point below 120° C. at a pressure of 1,013 mbar;
      (a2) at least one peroxide as polymerization initiator; and
      (a3) as polymerization co-accelerator, at least one amidine; and
   (b) paste B contains
      (b1) at least one monomer for radical polymerization with a boiling point below 120° C. at a pressure of 1,013 mbar;
      (b2) at least one heavy metal compound as polymerization accelerator; and
      (b3) as polymerization co-accelerator, at least one sulfimide;
   wherein at least one of the pastes A and B contains, as component (a4) and/or (b4), at least one filling agent that is insoluble in (a1) and/or (b1), respectively.

2. The kit according to claim 1, wherein the at least one monomer (a1) and/or (b1) for radical polymerization is a methacrylate monomer.

3. The kit according to claim 1, wherein paste A and paste B contain an amount of the at least one monomer (a1) and/or (b1) for radical polymerization in a range of 15 to 85% by weight, each relative to the total weight of paste A and/or paste B, respectively.

4. The kit according to claim 1, wherein the at least one peroxide (a2) has a half-life >10 hours at 70° C.

5. The kit according to claim 4, wherein the at least one peroxide (a2) is selected from the group consisting of cumene-hydroperoxide, 1,1,3,3-tetramethylbutyl-hydroperoxide, t-butyl-hydroperoxide, t-amyl-hydroperoxide, di-isopropylbenzen-mono-hydroperoxide, di-t-butylperoxide, dicumylperoxide, and t-butylcumyl-peroxide.

6. The kit according to claim 1, wherein paste A contains an amount of the at least one peroxide (a2) in a range of 0.01 to 10% by weight, relative to the total weight of paste A.

7. The kit according to claim 1, wherein paste A contains an amount of the polymerization co-accelerator (a3) in a range of 0.1 to 20% by weight, relative to the total weight of paste A.

8. The kit according to claim 1, wherein the at least one heavy metal compound (b2) is selected from the group consisting of copper(II) hydroxide, copper(II) metharylate, copper(II) acetylacetonate, copper(II) 2-ethyl-hexanoate, cobalt(II) hydroxide, cobalt(II) 2-ethyl-hexanoate, and basic copper(II) carbonate.

9. The kit according to claim 1, wherein paste B contains an amount of the at least one heavy metal compound (b2) in a range of 0.0005 to 0.5% by weight, relative to the total weight of paste B.

10. The kit according to claim 1, wherein the at least one sulfimide (b3) is saccharine.

11. The kit according to claim 1, wherein paste B contains an amount of the polymerization co-accelerator (b3) in a range of 0.1 to 10% by weight, relative to the total weight of paste B.

12. The kit according to claim 1, wherein the at least one filling agent (a4) and/or (b4) that is insoluble in (a1) and/or (b1), respectively, is a particulate polymer.

13. The kit according to claim 1, wherein the at least one filling agent (a4) and/or (b4) that is insoluble in (a1) and/or (b1), respectively, is an insoluble polymer selected from the group consisting of cross-linked poly(methylmethacrylate-co-methylacrylate), cross-linked poly(methylmethacrylate), and a mixture of said two polymers.

14. The kit according to claim 1, wherein paste A, paste B or paste A and paste B contain a polymer (a5) and/or (b5) that is soluble in (a1) and/or (b1), respectively.

15. The kit according to claim 14, wherein the polymer (a5) and/or (b5) that is soluble in (a1) and/or (b1), respectively, is selected from the group consisting of poly(methacrylic acid methylester), poly(methacrylic acid ethylester), poly-(methylmethacrylic acid propylester), poly(methacrylic acid isopropylester), poly(methylmethacrylate-co-methylacrylate), and poly(styrene-co-methyl methacrylate).

16. A method for producing a paste for mechanical fixation of articular prostheses, for covering skull defects, for filling bone cavities, for femuroplasty, for vertebroplasty, for kyphoplasty, for the manufacture of spacers or for the production of carrier materials for local antibiotics therapy, wherein said paste is produced from the kit of claim 1.

17. A form body obtained through polymerization of a paste that obtained through mixing paste A and paste B of the kit of claim 1.

* * * * *